United States Patent [19]

Kastenhofer

[11] Patent Number: 5,447,231
[45] Date of Patent: Sep. 5, 1995

[54] PACKAGING FOR AN ELONGATED MEDICAL APPLIANCE

[75] Inventor: Gerhard Kastenhofer, Effretikon, Switzerland

[73] Assignee: Schneider (Europe) A.G., Bulach, Switzerland

[21] Appl. No.: 143,675

[22] Filed: Oct. 27, 1993

[30] Foreign Application Priority Data

Feb. 17, 1993 [EP] European Pat. Off. ......... 93102477

[51] Int. Cl.$^6$ ............................................ B65D 85/08
[52] U.S. Cl. .................................. 206/364; 206/363; 206/481
[58] Field of Search .................. 206/331, 363–365, 206/367, 368, 438, 461–463, 468, 476, 486–490, 481

[56] References Cited

U.S. PATENT DOCUMENTS

| | | |
|---|---|---|
| 1,949,161 | 2/1934 | Haug . |
| 2,947,415 | 8/1960 | Garth ................................. 206/364 |
| 2,962,161 | 11/1960 | Lacy ................................. 206/331 |
| 3,217,867 | 11/1965 | Harris ................................ 206/468 |
| 3,372,798 | 3/1968 | Thomas ............................. 206/364 |
| 3,417,866 | 12/1968 | Omer ................................. 206/488 |
| 3,891,088 | 6/1975 | Huebner ............................ 206/468 |
| 3,926,309 | 12/1975 | Center . |
| 3,930,580 | 1/1976 | Bazell et al. . |
| 3,967,728 | 7/1976 | Gordon et al. ..................... 206/438 |
| 4,062,239 | 12/1977 | Fowler et al. . |
| 4,142,632 | 3/1979 | Sandel ............................... 206/363 |
| 4,262,800 | 4/1981 | Nethercutt . |
| 4,779,727 | 10/1988 | Taterka et al. . |
| 4,828,108 | 5/1989 | Roth .................................. 206/368 |
| 5,131,537 | 7/1992 | Gonzales . |

FOREIGN PATENT DOCUMENTS

| | | |
|---|---|---|
| 0440427 | 8/1991 | European Pat. Off. . |
| 1283908 | 5/1963 | France . |
| 1439126 | 4/1966 | France . |
| 538966 | 8/1973 | Switzerland . |
| 1201303 | 8/1970 | United Kingdom ............... 206/462 |

*Primary Examiner*—Jimmy G. Foster
*Attorney, Agent, or Firm*—Peter C. Richardson; Lawrence C. Akers; Philip C. Strassburger

[57] ABSTRACT

A packaging comprises a sealed peel-apart flexible pouch in which the preshaped stem of a medical appliance is maintained by elastic pressure of the walls of a sheath open at its ends formed by a wall having two parallel lateral edges forming slides in which are engaged the lateral edges of two spaced apart portions of a second wall. The two walls are flat and deformable by their own elasticity. A retaining window is provided in one of the walls for a handling and connecting hub connected to the stem of the medical appliance to extend therethrough.

6 Claims, 4 Drawing Sheets

PACKAGING FOR AN ELONGATED MEDICAL APPLIANCE

BACKGROUND OF THE INVENTION

This invention relates to a packaging for an elongated medical appliance, such as for instance a catheter or a fiber optic surgical unit which have to be unpacked under sterile conditions, having at least a stem of predetermined shape connected to a handling and connecting hub, said packaging comprising a sealed peel-apart flexible pouch, an elongated support member inside the pouch, said support member being longer than the medical appliance, means for maintaining the stem and means for retaining the hub, said means for maintaining the stem and means for retaining the hub being capable to give way in order to permit withdrawal of the medical appliance.

The known packagings of that kind are designed to protect the medical appliance against the risks of contamination as well as those of shocks and deformation during storage and transit. They are also designed to facilitate withdrawal of the medical appliance in conditions appropriate to preserve sterility, in particular of the portions of the stem which have to be inserted into a patient, and to preserve as well the predetermined shape of the stem.

Within this frame, the sealed flexible pouch protects the medical appliance against the risks of contamination while the support member is intended to maintain the medical appliance and to protect it against shocks, its length being greater than that of the medical appliance in order to avoid that the extremities thereof run through the flexible pouch.

The means for maintaining the stem and retaining the hub on the support member differ as they may be integrated to the support or partly integrated thereto and partly fitted in an adaptable piece essentially intended to maintain the shape of the stem.

When such means are integrated to the support member, they generally consist of grooves the contour of which corresponds to the contour of the stem, and the stem is maintained within these grooves by retaining tongues respectively located on both sides of such grooves, which tongues give way to the stem upon raising thereof. The support member also comprises a hollow housing in which the hub is immobilized in the plane of the support member, withdrawal of the hub being achieved by merely lifting it. Of course, there is needed a different support member for each different shape of the stem and hub.

Upon use of the medical appliance, one person first peels apart the pouch at least up to the level of the hub; another person then grasps the hub and lifts it out of its housing and then extracts the stem from the grooves by pulling it while the first person firmly holds the support member. This operation is relatively difficult to perform and requires quite a good touch to avoid damaging the stem. In addition, on the side opposite to the support member, the stem as well as the hub are not protected against shocks, either during storage or transit or further handling because they are only covered by the flexible pouch.

U.S. Pat. No. 4,779,727 discloses a packaging for a catheter, having a tray and an interchangeable insert located in a recess of the tray. The tray and the insert comprise each a plurality of grooves provided with retaining tabs, and at least one of the grooves of the insert is in line with a groove in the tray for holding a catheter therein. Each groove in the tray is provided with a hub retaining slot. Apart from the fact that it is possible to change the insert in order to accommodate different catheters, the problems are the same as outlined herebefore.

European Patent Application published under No. 0440427A1 discloses a packaging including a tray for accommodating the hub and shaft of a catheter and a curve retention insert for securely retaining a curve portion of the catheter; in order to facilitate the extraction of the catheter, the insert is slidably mounted along the longitudinal axis of the tray and the catheter shaft as well as the curve portion are located in corresponding tracks where they are retained in place by tabs providing a snap-fit retention. Both the tray and the insert are provided with conformations allowing relative immobilization thereof during storage and transit as well as relative mobility thereof upon grasping the hub and pulling it laterally out of the packaging. On this traction movement, the shaft of the catheter begins to slide in its track bringing with it the curve retention insert which slides along the tray up to raising the catheter shaft within its track until it snaps out from beneath the tabs; at this point the catheter shaft and the insert can be removed from the tray, and subsequently the catheter curve can be removed from the insert. As for the previously described materials, there is a substantial risk of damage due to forced extraction from a snap-fit retention arrangement. And here again the catheter is not protected against shocks on the side opposite to the tray and its insert because they are only covered by the pouch.

U.S. Pat. No. 4,262,800 describes a holder for a delicate medical instrument such as a surgical unit, comprising an outline of the instrument, pairs of retainer pegs located about the outline, and elastic bands engaging the pegs to secure the instrument on the holder. This arrangement reduces the risk of damaging the medical instrument upon pulling thereon in order to withdraw it from the holder. However, there is the risk of having the elastic bands flying off in all directions upon pulling on the instrument and it is therefore preferable to take them off one by one before using the instrument. This document outlines, as the previous ones, the importance of the problem of maintaining and freeing the shafts, and more particularly the curved portions of medical appliances such as catheters and the like.

U.S. Pat. No. 3,926,309 describes a two layer packaging for separate articles such as a catheter, disposable glove and rinse container. A plastic sheet is folded to bring its two opposite side edges adjacent, and each end of the folded sheet is sealed to form a first pouch. A closure sheet overlying the plastic sheet including the area in which the two opposite side edges are disposed is then sealed about the perimeter to the first sheet to form a second pouch adjacent the first one. A catheter lies in an unrestrained state in the first pouch and other materials such as a disposable glove and rinse container may lie in the second pouch. It may be noted that there is no means for maintaining and protecting the shape, possibly curved, of the catheter.

In order to unpack the catheter it is necessary to first tear the closure sheet to unseal the first pouch and remove the disposable glove and rinse container, and then to separate the opposite side edges of the folded sheet forming the first pouch to provide access into the pouch and grasp the catheter for removing it from the pouch. Here, shock protection of the catheter is somewhat better but removal of the catheter is not too easy and may cause deformations and damage.

The object of this invention is to seek to simply and economically solve the problems relating to maintaining a medical appliance, to protecting it against shocks during storage and transit, and to removing it from its packaging.

SUMMARY OF THE INVENTION

According to the invention, there is provided a packaging for an elongated medical appliance having at least a stem of predetermined shape connected to a handling and connecting hub, said packaging comprising a sealed peel-apart flexible pouch, an elongated support member inside the pouch, said support member being longer than the medical appliance, means for maintaining the stem and means for retaining the hub, said means for maintaining the stem and means for retaining the hub being capable to give way in order to permit withdrawal of the medical appliance, characterized in that the support member is a sheath with open ends formed by two flat walls which are superposed and deformable by their own elasticity, which walls are connected to each other at their lateral edges, said walls being at a distance from one another which is smaller than the minimal thickness of the stem of the medical appliance, and said sheath having on at least one of said two flat walls a retaining window for partly housing the hub.

In that way, during storage, transit and handling, the stem of the packaged medical appliance, be it with or without a curved tip, is maintained between the two walls by a pressure resulting from the elastic deformation of said walls which is caused by the thickness of the stem which is greater than the distance between the walls when at rest. On the other hand, the part housing of the hub in the window of the sheath prevents the hub from moving in the longitudinal direction of the sheath. Furthermore, as the medical appliance is located between the two flat walls, there is a sufficient protection against shocks identical on both sides of the sheath, and the flexible pouch which surrounds the hole has no other function than assuring the protection of the medical appliance against contamination and, where needed, the labelling of the product.

Upon usage, the medical appliance can be withdrawn from the packaging without any risk of damage or deformation of its stem. As a matter of fact, after having peeled back a portion of the flexible pouch, the nurse squeezes the two lateral edges of the sheath in order to bring them closer to one another, which causes the two flat walls to bulge outwardly by elastic deformation, thus freeing the stem of the medical appliance from the retaining pressure to which it was submitted between the said walls. The doctor may then easily withdraw the medical appliance from the sheath.

According to a first embodiment of the invention, a first wall of the sheath has its lateral edges forming slides in which the two corresponding lateral edges of the second wall are slidingly engaged, said second wall being provided with the hub retaining window. After the opening of the flexible pouch up to the hub location and the release of the stem retaining pressure by the nurse as outlined hereabove, the doctor draws the medical appliance by the hub while carrying with it the second wall along the slides of the first wall up to the end of the first wall, at which time he can grasp the said hub from the other side of the second wall, disengage the hub from the window, and then easily withdraw the stem from the sheath.

According to a second embodiment, the second wall of the sheath, also slidably engaged by its edges in lateral slides of the first wall, is divided in two portions with a transverse spacing between them forming the window partly housing the hub. In this arrangement, when the hub drawn by the doctor reaches the edge of the first wall, the portion of the second wall located opposite to the stem falls and frees the hub. The doctor therefore does not have to grasp the hub from the other side for withdrawing the stem from the sheath. As an alternative, the nurse may only peel back the flexible pouch a small distance below the upper border of the walls of the sheath, then the doctor takes away the portion of the second wall located opposite to the stem and throws it away, whereby he may then simply grasp the medical appliance by its upper end and pull it out from the packaging.

According to a third embodiment, the two walls of the sheath are connected to each other at their lateral edges so as to form one single piece the cross section of which is a continuous contour, and the two walls thus connected have each a hub housing window, the window of one of the walls being equal to and superposed to the window of the other wall. In this case, the nurse needs only to open the flexible pouch at the end opposed to the stem and to squeeze the lateral edges of the sheath to sufficiently bulge the two walls in order to simultaneously release the stem and the hub from their respective retention. The nurse then inclines the sheath so as to make gently slide the hub into the hand of the doctor who can fully withdraw the medical appliance from the packaging.

According to a fourth embodiment, the sheath with a continuous contour cross section of the third embodiment is divided in two parts nesting one into the other in their longitudinal direction, and at least one of the walls of these two portions comprises at one of its ends an open cut forming the hub housing window upon fitting in one of the said two portions. In this embodiment, the method of withdrawing the medical appliance does not require any preliminary sliding out of the sheath. After opening the flexible pouch up to the level of the hub, the nurse uncouples and takes away the accessible portion of the sheath squeezing its lateral edges, and the doctor then grasps the hub thus released from its retention and draws the stem from the other portion of the sheath while the nurse squeezes that other portion to release the stem from the pressure of the two walls.

In these four embodiments as well as in variants thereof which will appear in the following description, the sheath provides the means for maintaining the stem as well as the means for retaining the hub, which results in a great simplicity of realization. The system also avoids the need of having any kind of recessed shaping in a support member specifically adapted to maintain the stem of a medical appliance. As all the usual shapes of the stem can be so maintained, the packaging according to the invention can be said to be practically universal.

BRIEF DESCRIPTION OF THE DRAWINGS

The invention will now be described more particularly with reference to the accompanying drawings which show, by way of example only, four embodiments of the invention.

In the drawings.

DETAILED DESCRIPTION OF THE INVENTION

Figure 1:
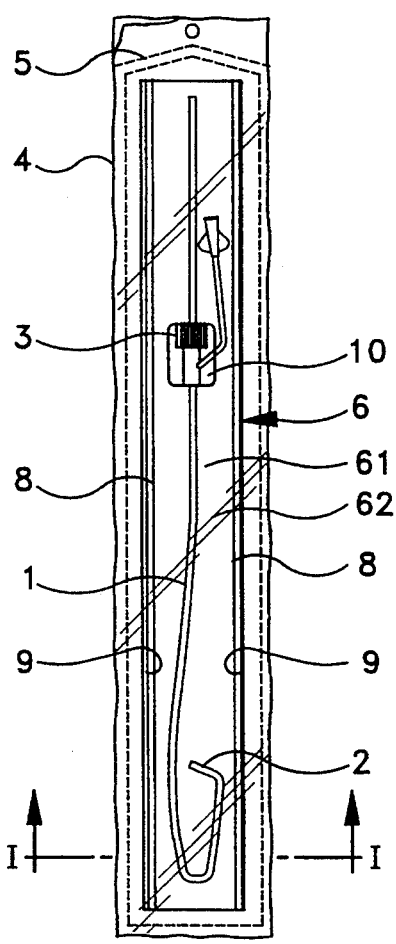
FIG. 1 is a plan view of the first embodiment.

The first embodiment of the packaging shown in FIG. 1 is for a catheter comprising a stem 1 with preshaped tip 2 and a handling and connecting hub 3 connected to the stem 1.

The packaging comprises a peel-apart flexible pouch 4 formed of two superposed sheets which are sealed to each other along their peripheral edges, as shown by dotted line 5, inside which is enclosed a sheath 6 with open ends. The sheath 6, longer than the catheter, is formed by two flat superposed walls 61 and 62 which are deformable by their own elasticity, and which are clearly shown in FIG. 2. Wall 61 comprises two lateral parallel edges forming slides 8, and wall 62 comprises two lateral parallel edges 9 engaged into and maintained by the two slides 8. The slides 8 are each made here by a turned down U shaped fold in each of the two edges of wall 61.

Figure 2:
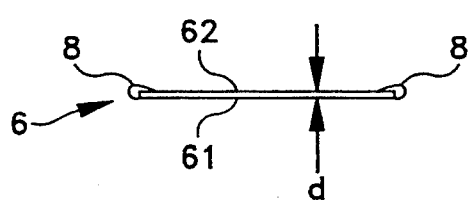
FIG. 2 is a transverse section of the assembly of two elements of the first embodiment.

The slides 8 are made in such a manner that they maintain the two walls 61 and 62 at a distance -d- from one another which is smaller than the minimal thickness of the stem 1 and tip 2 of the catheter, before installation of the latter between the walls 61 and 62 as shown in FIG. 2.

Wall 62 has a window 10 in which the hub 3 of the catheter is engaged, as shown in FIG. 1, in order to immobilize the catheter in the longitudinal direction of the sheath 6; thus, the catheter cannot bump against the ends of the flexible pouch 4 and damage them during storage, transit or handling.

The materials constituting the flexible pouch 4 and the sheath 6 can be fully transparent or partly opaque and partly transparent, depending on the need of labelling the medical appliance or of seeing it through wall 62.

Figure 3:
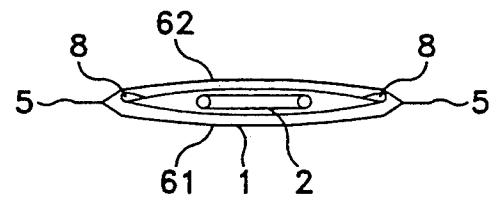
FIG. 3 is a transverse section along line I—I of FIG. 1.

The packaging with its flexible pouch 4 and the stem 1 and its preshaped tip 2 maintained between the two walls of the sheath 6 are shown in the transverse section of FIG. 3. This section shows clearly that stem 1 and preshaped tip 2 are maintained by the elastic deformation of the flat walls of the sheath 6, this being due to the retaining action of the lateral slides 8 and to the thickness of the stem 1 and preshaped tip 2 which is greater than the distance -d- separating walls 61 and 62. The pressure resulting from that deformation maintains the stem 1 and its tip 2 in place, and it also generates a retaining force for the two edges of wall 62 in the slides 8 of wall 61 in the longitudinal direction of the sheath. The synergy of these effects guarantees the viability of the packaging and of the positioning of the catheter in the packaging during storage and transit.

Figure 4:
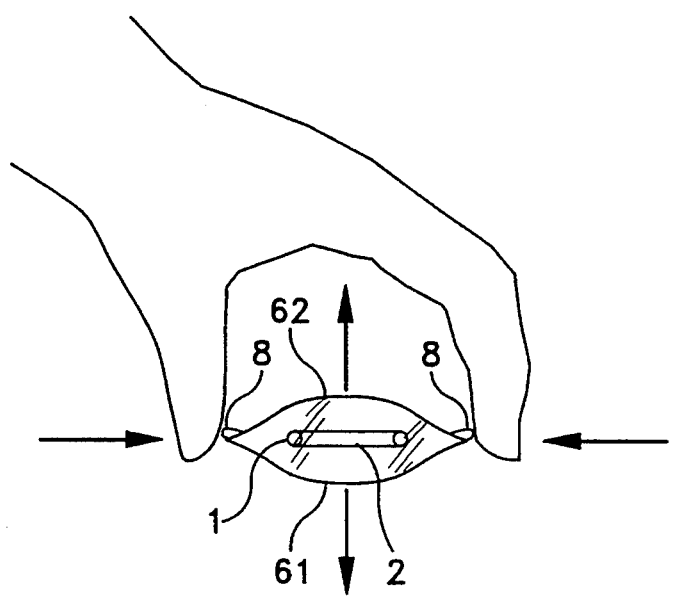
FIG. 4 shows a phase of the mode of use of the embodiment of FIG. 1.

FIG. 4 illustrates an important step of the withdrawal of the catheter from the packaging, as already explained hereinbefore and during which the nurse squeezes the slides 8 one towards the other with the result that the walls 61 and 62 of sheath 6 bulge outwardly and thereby release the stem 1 and tip 2 from the retaining pressure. This step, which can be a two hand operation above and below the window 10, may also permit freeing the hub 3 from the window 10 and allow sliding of the catheter on the side opposite the tip 2 up to having the hub 3 exiting the sheath 6 in order to be grasped by the doctor; this action would avoid the need for the doctor to move wall 62 along slides 8 of wall 61 by pulling on hub 3 when the thickness of hub 3 is not too great with respect to the width of the sheath.

Figure 5:
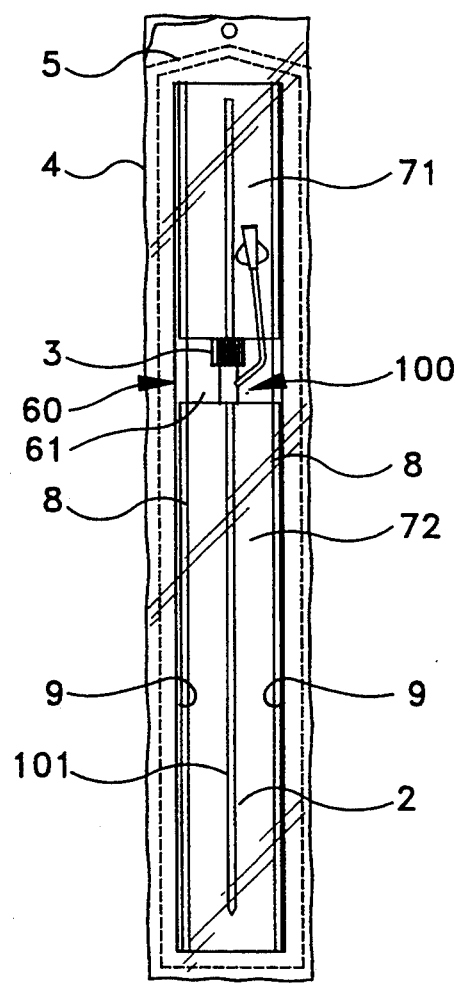
FIG. 5 is a plan view of the second embodiment.

In the second embodiment shown in FIG. 5, the sheath 60 comprises a wall 61 identical to that of the first embodiment, including its two slides 8. The second wall 62 engaged in slides 8 is here divided in two portions 71 and 72 spaced apart from each other in the longitudinal direction of the sheath 6 and the space between these two portions forms the window 100 in which the hub 3 of a catheter with straight stem 101 is engaged and retained during storage and transit. By this particularly advantageous arrangement of the wall 62 of the sheath, the doctor needs only drawing the shortest portion 71.

Figure 6:
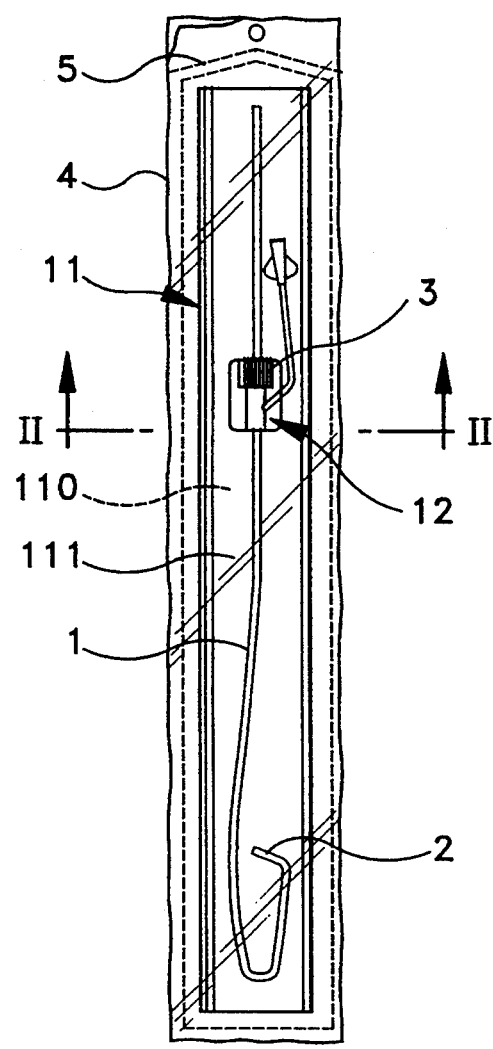
FIG. 6 is a plan view of the third embodiment.
Figure 7:
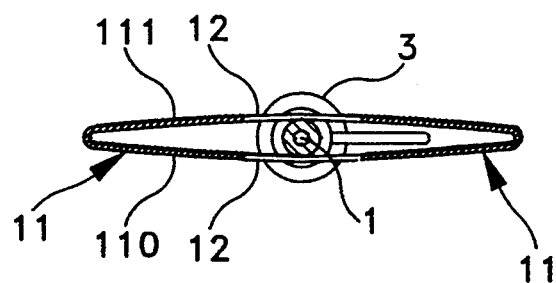
FIG. 7 is a section along line II—II of FIG. 6.

In the third embodiment shown in FIGS. 6 and 7 the two flat walls 110 and 111 of the sheath 11 connected by their edges form one single piece the cross section of which is a continuous contour as shown in FIG. 7. In this embodiment, the two walls 110 and 111 have each a window 12 equal and superposed to the window of the other wall, whereby the stem 1 of the medical appliance is pressed between these two walls as from its point of junction with the hub 3. To free the medical appliance, it is needed here to sufficiently bulge the two walls 110 and 111 in order to release the hub from the two windows 12.

Figure 8:
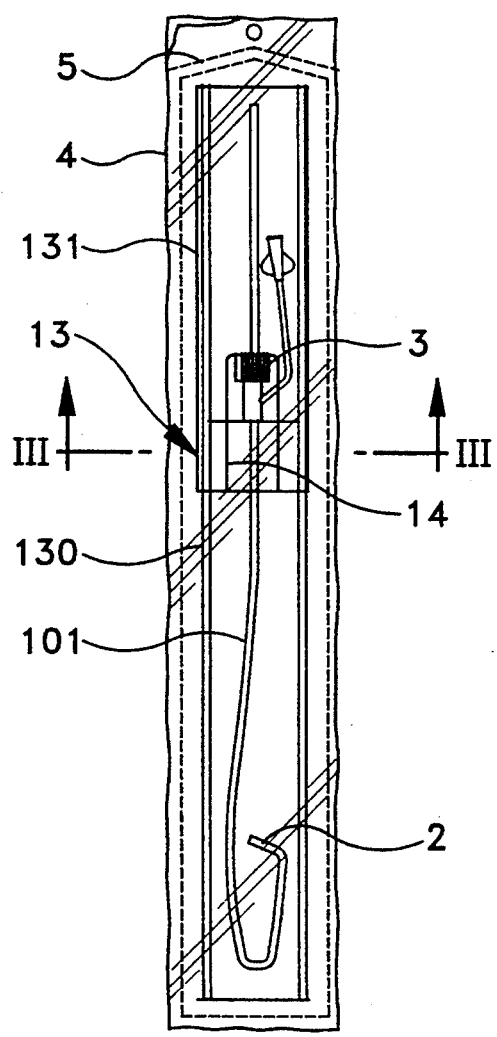
FIG. 8 is a plan view of the fourth embodiment.
Figure 9:
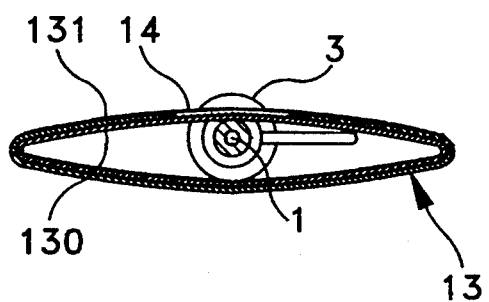
FIG. 9 is a section along line III—III of FIG. 8.

In the fourth embodiment shown in FIGS. 8 and 9, the sheath 13 also has a cross section which is a continuous contour. The sheath is divided here in two parts 130 and 131 nested one into the other in the longitudinal direction. One of the two walls of one of these parts, here upper part 131, comprises at one of its ends an open cut 14 forming the retaining window for housing the hub upon nested condition of the two parts of the sheath 13. Accordingly, after removal of the part with the open cut 14, the hub 3 of the catheter with straight stem 101 is released from its retaining.

As variants not shown of this fourth embodiment an open cut 14 may be made on each of the two walls of one of the parts 130 or 131 of the sheath 13, those cuts being equal and superposed; it is also possible to have such a cut on each of the two walls of the two parts of the sheath. These variants permit having the stem 101 pressed between the two walls as from its junction with the hub 3 and release of the retaining of the hub immediately after removal of one of the parts of the sheath.

In the third embodiment according to FIG. 6, it is also possible to have only one window 12 in one of the two walls 110 or 111.

In the first and second embodiments, the slides 8 may be made otherwise than as shown, for instance they may be structured as a profile extruded in the plastic material forming one of the walls. As regards the first embodiment, the hub retaining window can be on either of the first and second walls.

Of course, the catheter shown and the shapes of its stem and tip are not limitative and it has to be understood that the packaging according to the invention is applicable to any shape of the medical appliance.

I claim:

1. A package for a medical device comprising:
   (a) a first flexible wall having two side edges defining one side of the package;
   (b) a second flexible wall having two side slides along two lateral edges of the second flexible wall defining a second side of the package, the second flexible wall positioned along side the first flexible wall such that the two side slides slidably engage the two side edges of the first flexible wall; wherein at least one of the first flexible wall and the second flexible wall defines an opening; and
   (c) a medical device disposed in part between the first flexible wall and the second flexible wall, with a portion of the medical device extending through the opening.

2. The package of claim 1 wherein the two lateral side slides are U-shaped folds along the two lateral edges.

3. A package for a medical device, comprising:
   a first flexible wall having two side edges defining one side of the package;
   a second flexible wall having two side slides along two lateral edges of the second flexible wall defining a second side of the package, the second flexible wall positioned along side the first flexible wall such that the two side slides slidably engage the two side edges of the first flexible wall; and
   wherein at least one of the first flexible wall and the second flexible wall is defined by two separate spaced apart sheets, the space between the two separate sheets allowing a portion of the medical device to extend therethrough.

4. The package of claim 3 wherein the two lateral side slides are U-shaped folds along the two lateral edges.

5. A package for a catheter, comprising: a flexible hollow tube defining a space for receiving a catheter therein, the catheter having a hub, wherein the space, prior to insertion of the catheter, has a height less than the thickness of the catheter to be contained therein, the flexible hollow tube having a medial portion defining an opening to allow a portion of the catheter to extend therethrough; and a catheter disposed longitudinally in the package, the catheter disposed in major part in the space defined by the flexible hollow tube, with a portion of the catheter hub extending through the opening.

6. A package for a catheter, comprising: a first flexible hollow tube and a second flexible hollow tube, each flexible hollow tube defining a space for receiving a catheter therein, the catheter having a hub, wherein each space, prior to insertion of the catheter, has a height less than the thickness of the catheter contained therein, at least one of the tubes defining a cut out, wherein the first and second flexible hollow tubes are at least partially configured one inside the other to thereby define an opening to allow a portion of the catheter to extend therethrough; and further comprising a catheter disposed in major part in the space defined by the first and second tubes, with a portion of the catheter hub extending through the opening.

* * * * *